United States Patent [19]

West et al.

[11] 4,212,205

[45] Jul. 15, 1980

[54] CONTAINER DEFECT DETECTION APPARATUS

[75] Inventors: Perry C. West, Saratoga; Robert R. Buss, Palo Alto, both of Calif.

[73] Assignee: Reticon Corporation, Sunnyvale, Calif.

[21] Appl. No.: 11,497

[22] Filed: Feb. 12, 1979

[51] Int. Cl.³ .............................................. G01N 29/04
[52] U.S. Cl. ........................................ 73/579; 73/52
[58] Field of Search ..................... 73/579, 52; 209/590

[56] References Cited

U.S. PATENT DOCUMENTS

| | | | |
|---|---|---|---|
| 3,438,493 | 4/1969 | Goble | 73/579 |
| 3,802,252 | 4/1974 | Hayward et al. | 73/52 |

*Primary Examiner*—Anthony V. Ciarlante
*Attorney, Agent, or Firm*—Blakely, Sokoloff, Taylor & Zafman

[57] ABSTRACT

An apparatus for detecting defects in empty containers, such as dents in cans, is disclosed. The containers are magnetically struck, causing them to ring at their natural frequencies. A microphone senses this resonance; a bandpass filter filters out the known frequencies generated by an acceptable container. The energy associated with other frequencies is examined to detect defects in the containers. A circuit for reducing the effects of background acoustic noise and a circuit for sensing the amount of energy imparted to the container when it is struck are also disclosed.

13 Claims, 3 Drawing Figures

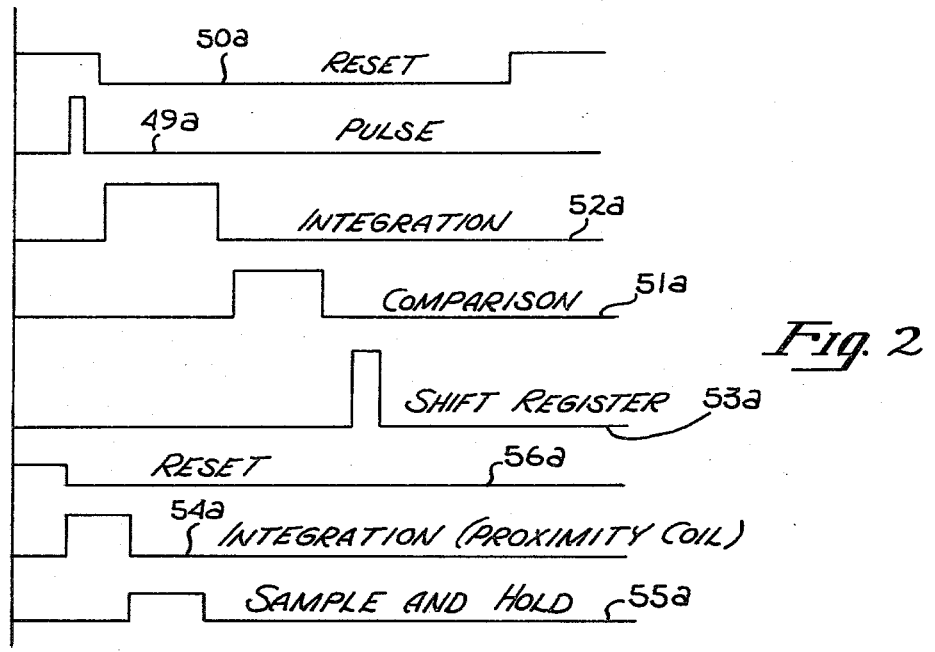
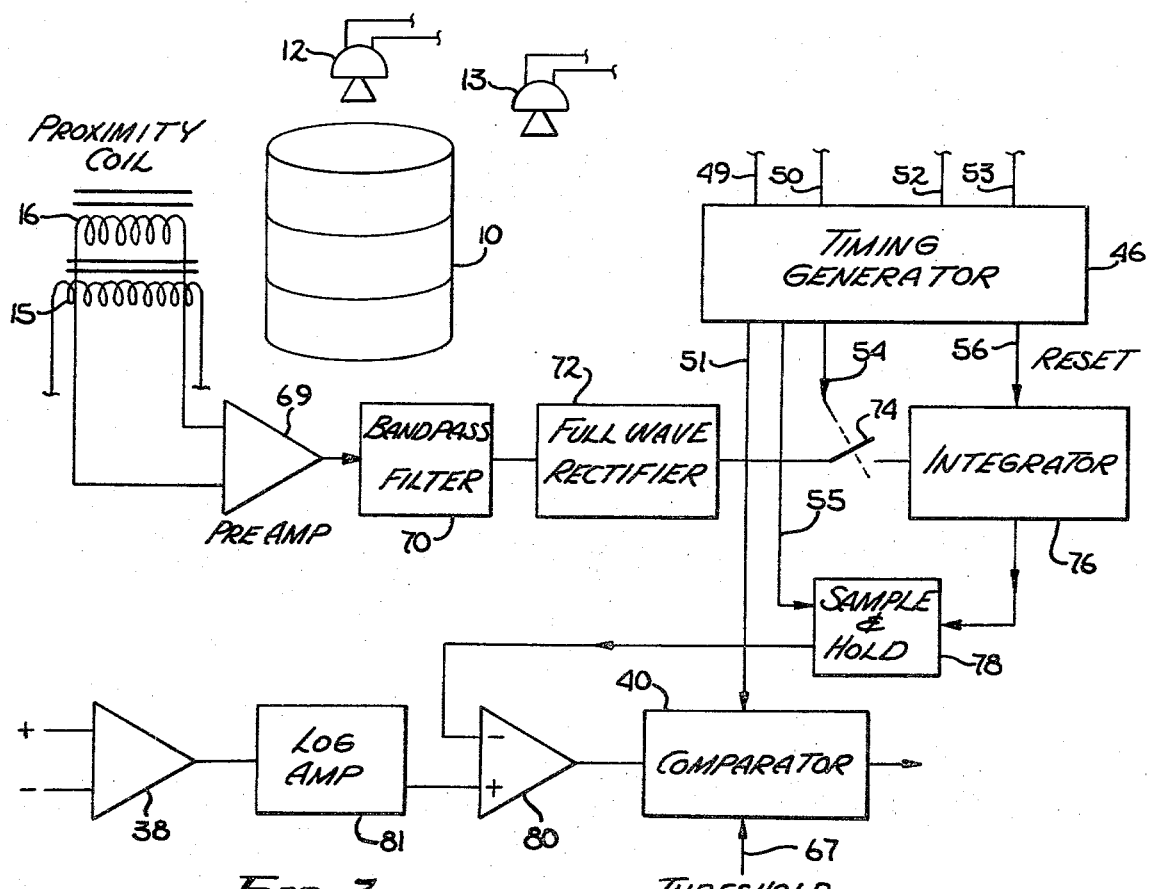

CONTAINER DEFECT DETECTION APPARATUS

BACKGROUND OF THE INVENTION

1. Field of the Invention

The invention relates to the field of the detection of defects in containers, particularly dents in metal containers.

2. Prior Art

Prior to the filling of containers such as steel and aluminum cans, it is desirable to know if the cans are dented or otherwise deformed. Defective containers, if filled and delivered to retail outlets, are often returned by retailers since consumers find them unacceptable. Moreover, severe dents or deformation in the containers can result in their failure when they are filled and sealed.

There are a number of difficult problems associated with the acoustic examination of containers. In a typical container manufacturing or container filling environment, empty or substantially empty containers are moved along a conveyor. The metal containers, because of this movement, cause a great deal of noise. This noise makes it difficult to acoustically examine the containers in the environment where such examination is most expedient. Thus consideration must be given to this background noise for the reliable detection of defects. Also, when containers are moved on a conveyor they are not perfectly aligned and therefore the position of a container under test varies from container to container. When these containers are acoustically examined the amount of energy imparted to a container when it is struck becomes important. Mechanical alignment of these containers or mechanical position detectors are complicated and costly. Means are required to compensate for this positioning problem.

As will be seen, the present invention provides an apparatus for acoustically detecting defects in containers. The problems associated with a noisy environment and the fact that the precise position of a container is not known are solved.

The closest prior art known to Applicant is described in U.S. Pat. No. 3,802,252. The apparatus described in this patent detects the internal pressure of a sealed container. This information is used to determine overpressurization in aerosol cans, volume of liquid sealed within a can, and also aids in detecting spoilage of food products sealed in containers. The containers are magnetically struck and their frequency response examined since the acoustic "ping" is a function of internal pressure. This patent does not describe any apparatus for detecting dents or deformation in open containers.

SUMMARY OF THE INVENTION

An apparatus for detecting defects in an open container is described. The container, such as a can, is magnetically struck, causing it to vibrate at its natural frequencies. A sensing means such as a microphone is disposed above the container to sense the resonant vibrations of the container. A filter is coupled to the sensing means for selecting predetermined frequencies associated with defective containers. The energy associated with these frequencies is examined and compared with a threshold level to detect defects. In this manner, by way of example, dents of approximately $\frac{1}{8}$-inch are detected, allowing the containers to be discarded before filling.

BRIEF DESCRIPTION OF THE DRAWINGS

FIG. 2 is a timing diagram illustrating various timing signals associated with the invented apparatus.

FIG. 3 is a block diagram of the portion of the apparatus used to detect the amount of energy imparted to a container when it is struck.

Figure 1:
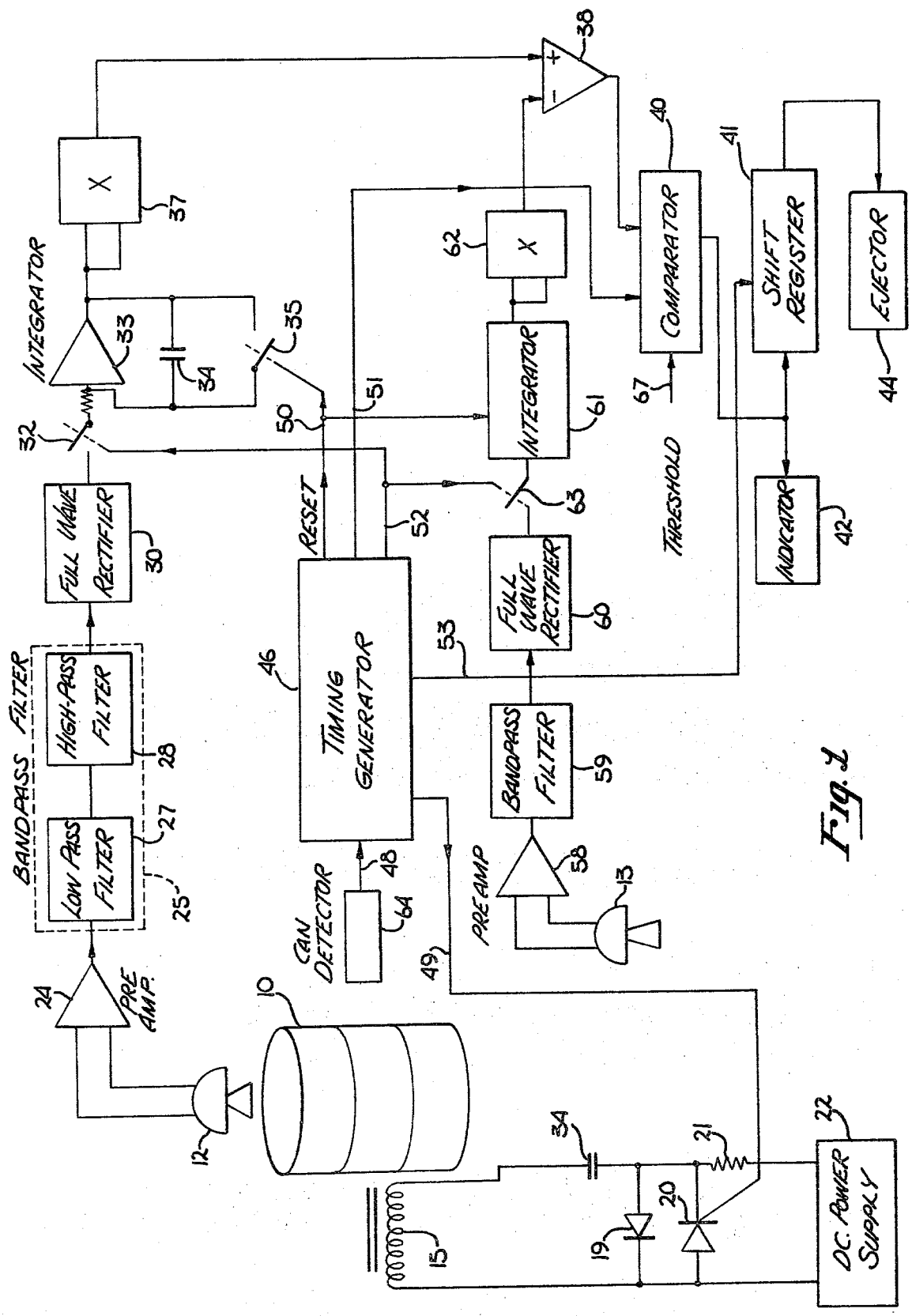
FIG. 1 is a block diagram and partial schematic of the presently preferred embodiment of the invented apparatus and includes a block diagram of the background noise cancellation circuit.

DETAILED DESCRIPTION OF THE INVENTION:

An apparatus for detecting defects in open containers, such as dents in steel and aluminum cans, is described. In the following description, numerous specific details are set forth, such as specific frequencies, in order to provide a thorough understanding of the present invention. However, it will be obvious to one skilled in the art that the invention may be practiced without these specific details. In other cases, wellknown circuits have been shown in block diagram form in order not to obscure the present invention in unnecessary detail.

Referring first to FIG. 1, a can 10, which may be any container such as an aluminum or steel can, is shown disposed below a microphone 12 and adjacent to a coil 15. In the environment in which the apparatus is employed, the can 10 is on a conveyor and is moved adjacent to the microphone 12 and coil 15 by the movement of the conveyor. For purposes of simplification, the conveyor is not illustrated.

A can detector 64, which in the presently preferred embodiment is an optical detector, detects the can 10 when the can is below the fixed microphone 12 and adjacent to the fixed coil 15. This detector provides a signal to the timing generator 46 on line 48 to initiate the detection of dents in the can 10. Any one of a plurality of well-known detection means may be employed for the can detector 64.

When the can is in position to be tested, as determined by the detector 64, it is struck by a magnetic field from the exciter coil 15 to cause the can to ring at its natural frequencies. The coil 15 is coupled in series with a capacitor 34; a diode 19 and an SCR 20 are coupled in opposite directions across the capacitor and coil. The diodes are coupled to a DC power supply 22 through a resistor 21. This DC supply provides a high direct current potential to the circuit which includes the coil 15.

For purposes of discussion, assume that the can 10 is a drawn steel can having a diameter of approximately $2\frac{5}{8}$ inches and a height of approximately $4\frac{1}{2}$ inches. Assume further that such a container, without dents, has a fundamental resonant frequency of between 500 and 800 Hz. The container also resonates with a strong fourth harmonic which falls within the range of between 2,000 and 3,200 Hz. As presently implemented, the coil 15 magnetically strikes the can 10 with a single cycle of approximately 3.0 kHz. This frequency is above the natural frequency of the can 10; however, it causes the can to ring at its natural frequencies. In the presently preferred embodiment, the coil 15 has an inductance of 281 $\mu$h and the capacitor 34 a capacitance of 10 $\mu$F. The coil is activated, as will be described later, by a signal applied to the gate of the SCR 20 on line 49.

The vertical location of the coil 15 along the can 10 has not been found to be critical, except that the apparatus has been found not to operate well when the coil is at the bottom of the can. In the presently preferred embodiment, the coil is approximately ⅓ the vertical height up the can from the bottom of the can. It should be noted that the magnetic field from the coil 15 induces eddy currents in the can causing it to ring. Thus, substantially the same ringing is obtained with a (non-ferromagnetic) aluminum can. While in the presently preferred embodiment the can is struck with a magnetic field from the coil 15, other means may be employed to strike the can, such as mechanical means.

The microphone 12 disposed above the can 10 may be an ordinary dynamic microphone, a condenser microphone or other suitable transducer. In the presently preferred embodiment, this microphone has a dynamic range of between 15 Hz and 15 kHz. The output of the microphone 12 is coupled to a preamplifier 24. Other sensing means, such as an optical detector to detect the physical vibrations, may be used in place of the microphone. However, the vibrations are of such small amplitude as to make acoustic detection generally more sensitive and simple.

The signal from the microphone 12, after preamplification, is passed through a bandpass filter 25. This filter is used to select predetermined frequencies associated with a defective (dented) container. For the described container, filter 25 has a bandpass between the fundamental frequency of the container and its fourth harmonic. As presently implemented, a low-pass filter 27 and a high-pass filter 28 are employed to obtain the bandpass. The low-pass filter 27 passes frequencies below 2,000 Hz and the high-pass filter 28 has a low frequency cutoff at 800 Hz. Both these filters are ordinary active filters providing an 18 dB per octave rolloff.

For each size and shape container to be tested, the resonant frequencies of the container (without dents) are first determined, for example, empirically. Defective (dented) containers are likewise struck to determine the resonance of these containers. The frequency band or bands having the greatest difference in amplitudes between the acceptable and non-acceptable containers are then determined. In this manner an optimum frequency band or bands is established. For the above-described can, it has been found that dented cans have substantially more resonance between the fundamental and fourth harmonic than do acceptable cans. For this reason, the frequency band between this fundamental and fourth harmonic is used to detect defects. Filter 25 selects this optimum band for the described can.

The output of the bandpass filter 25 is coupled to the input of a fullwave rectifier 30. An ordinary fullwave, active rectifier is employed, in the presently preferred embodiment. The output of the rectifier 30 is coupled to an integrator through a switch 32. The switch 32 is activated by a signal received from the timing generator 46 on line 52.

The integrator in the presently preferred embodiment is an active integrator. The integration occurs on the capacitor 34 which is coupled between the input and the output of the operational amplifier 33. A switch 35 is coupled across capacitor 34 to permit the discharging of the capacitor 34, that is, the resetting of the integrator. The switch 35 is controlled by a timing signal received from the generator 46 on line 50.

The magnitude of the output from the integrator, which is a DC signal, is squared. In the presently preferred embodiment, the output of the integrator is coupled to the two input terminals of a multiplier 37 to perform this squaring, with the output of the multiplier 37 coupled to the positive input terminal of a differencing amplifier 38. As will be described, the squaring performed by the multiplier 37 and the multiplier 62 is used as part of the background noise rejection system.

In the presently preferred embodiment, a second microphone 13, which may be identical to the microphone 12, is mounted spaced-apart from the microphone 12 to sense background noise. The spatial displacement between the microphones may not be critical and in one environment a displacement of 6 inches has been found to be satisfactory. The output of the microphone 13 is processed in an identical manner to the signal from microphone 12. The output of the microphone is coupled to a preamplifier 58 which may be identical to preamplifier 24. The output of the preamplifier 58 is coupled to a bandpass filter 59 which has the same characteristics as bandpass filter 25. A fullwave rectifier 60 is used to rectify the output of the bandpass filter 59 and this rectifier may be identical to the rectifier 30. The rectifier is coupled to an integrator 61 which has the same characteristics as the integrator associated with capacitor 34. A switch 63 corresponding to switch 32 interconnects the rectifier 60 with the integrator 61. The magnitude of the output from the integrator 61 is squared through the multiplier 62. The output of the multiplier 62 is coupled to the negative input terminal of the differencing amplifier 38. The reset signal on line 50 is coupled to the integrator 61 and the signal on line 52 is used to activate switch 63 in the same manner as that signal is used to activate the switch 32.

The squared signals from the multipliers 37 and 62 are differenced within the amplifier 38. The output of this amplifier is coupled to a comparator 40.

The comparator 40 is employed to compare the output of the amplifier 38 with a predetermined threshold value applied to the comparator on line 67. This comparison occurs when the comparator receives a timing signal on line 51 from the timing generator 46. In the presently preferred embodiment, the threshold level applied to the comparator 40 is set once the apparatus has been installed. The threshold level establishes the size of dents or amount of deformation which is rejected. When the output of the amplifier 38 exceeds the threshold voltage on line 67, the comparator 40 produces an output signal which is coupled both to a shift register 41 and to an indicator 42; otherwise no outputs occur from the comparator. The indicator 42 provides a visual or audible indication of a defective can. The signals from the comparator 40 are shifted along the shift register 41 on command of timing signals from the generator 46 (line 53). The output from the shift register 41 is coupled to a mechanical ejector 44 which, in the preferred embodiment, is used to eject defective cans from the conveyor.

Assume that the can detector 64 has detected the presence of the can 10 below the microphone 12 and adjacent to the coil 15. The signal communicated to the timing generator 46 on line 48 initiates a testing cycle. When the signal on line 48 is received by the generator, the generator 46 produces a pulse on line 49. This pulse is shown in FIG. 2 on line 49a. The pulse when communicated to the SCR 20 causes this device to conduct, discharging the capacitor 34. Note that prior to the time that the pulse is delivered to the SCR 20, the capacitor 34 is charged to the output potential of the supply 22. The capacitor 34 discharges through the coil 15 and the SCR 20, providing a half-cycle of approximately 3 kHz current. When the discharge of the capacitor is completed, the SCR 20 turns-off and the capacitor 34 is recharged through the coil 15 and the diode 19. This provides the second half-cycle of current through the coil 15.

As presently implemented, after the can has been struck, the signal 50a shown in FIG. 2 is coupled to the switch 35 opening the switch so that a charge may be accumulated on the capacitor 34. Then, or simultaneously with the opening of the switch 35, the switch 32 is closed by a signal provided on line 52. As presently implemented, approximately 5 ms lapse occurs between the time that the can is struck and the time that the switch 32 is closed. The signals associated with resonance between the fundamental frequency and fourth harmonic are integrated. This integration continues for a period of approximately 30 ms before the comparator 40 is activated. The waveforms for the signals on lines 51 and 52 are shown in FIG. 2 as signals 51a and 52a, respectively. Ignoring for a moment the signal from the multiplier 62, the output of the amplifier 38 is compared with the threshold level on line 67. If sufficient energy in the frequency band between 800 and 2000 Hz for the described can is present, then a defective can has been detected and a signal is coupled to the indicator 42 and the shift register 41.

After the comparison has occurred, the contents of the shift register are shifted along the register 41. The register 41 may be clocked by a signal from the conveyor or by a signal which occurs at the end of the testing cycle as shown by the signal on line 53a of FIG. 2. The shift register 41 is used to provide a delay between the time that a defective can is sensed and the time that the ejector 44 is activated. This is used since the mechanical ejector is typically spaced-apart from the can under test.

As is apparent from the waveforms shown in FIG. 2, the timing generator 46 may be fabricated from commercially available components using well-known circuit technology to provide the waveforms of FIG. 2.

The path consisting of microphone 13, preamplifier 58, filter 59, rectifier 60, switch 63, integrator 61 and multiplier 62 performs in the same manner as the main path disposed between the microphone 12 and the multiplier 37. The output from the multiplier 62 is subtracted from the main path signal within the differencing amplifier 38. The microphone 13 senses the background noise; however, since it is not disposed over the can 10, it does not sense to any significant degree the ringing of the can. Note that the microphone 12 senses both the ringing of the can and the background noise. By subtracting the square of the background noise component in the amplifier 38 from the square of the component of the noise and the can's resonance, the noise component is substantially removed from the signal before the signal is applied to the comparator 40. It still may be desirable, in some applications, to mount both the microphones 12 and 13 in an acoustic enclosure disposed about the conveyor.

It has been found that by squaring the signals from the integrators prior to applying these signals to the differencing amplifier 38, a substantial gain in the noise cancellation is obtained. If the signal in the main path prior to being applied to multiplier 37 is represented by "a" and the signal in the background noise path is represented by "b" prior to the time that it is applied to the multiplier 62, the output from the amplifier 38 is equal to $a^2 - b^2$. This quantity may also be represented by $(a-b)(a=b)$. Thus, the same result may be achieved by subtracting a from b and by adding a and b and then multiplying the sum and difference signals. In this case, only a single multiplier is required with one differencing amplifier and one summing amplifier.

The energy imparted to the can 10 when struck by the coil 15 substantially affects the amount of energy sensed by the microphone 12 in the frequency band of interest. It has been empirically determined that the energy imparted to the can varies exponentially with the distance between the can and the coil 15. By way of example, in one particular measurement, the energy imparted to the can approximately doubled when the distance between the coil and can was changed from 0.150 inches to 0.025 inches. As mentioned, in a typical conveyor belt it is difficult to maintain consistent alignment of the cans and thus difficult to maintain a constant distance between the exciter coil 15 and can 10 for each strike. While mechanical means may be employed to maintain a constant distance, the electrical circuit of FIG. 3 is employed in the presently preferred embodiment to compensate for these distance variations.

In FIG. 3, the can 10 is again shown along with the microphones 12 and 13 and the excitor circuit 15. All the circuitry of FIG. 1 is employed, however is not shown in FIG. 3. A logarithmic amplifier 81 and a differencing amplifier 80 are disposed between the differential amplifier 38 and comparator 40 of FIG. 1 as part of the circuitry to compensate for the distance variations.

A second coil identified as proximity coil 16 is secured in fixed relationship to the coil 15 alongside the can 10. This second coil is oriented relative to coil 15 so as to provide a minimum magnetic coupling between these coils when no can is present. The output of this coil is coupled to a preamplifier 69. The output of the amplifier is coupled to a bandpass filter 70. Unlike the other bandpass filters, this bandpass filter has a much wider bandwidth. An ordinary RC filter is employed which has a low cutoff frequency lower than the fundamental frequency of the can and a high cutoff frequency higher than the fourth harmonic. This bandwidth is not critical. The output of the filter 70 is coupled to a fullwave rectifier 72 where it is fully rectified. A switch 74 and an integrator 76, which may be similar to switch 63 and integrator 61, respectively, are also employed to integrate the signal from the fullwave rectifier. A timing signal on line 54 controls the switch 74 and a timing signal on line 56 resets the integrator 76. The output of integrator 76 is passed through a sample-and-hold means 78 which samples the output of the integrator and holds that sample during the period of the comparison made by comparator 40. The signal on line 55 is used to activate the sample-and-hold means, causing it to sample the output of the integrator 76. Reset means (not shown) are employed to reset the sample-and-hold means after the completion of the comparison. The output of the sample-and-hold means 78 is subtracted from the signal from the logarithmic amplifier 81 and the resultant signal is used for the comparison.

Prior to the time that the pulse shown on line 49a of FIG. 2 activates the exciter coil 15, the integrator 76 is reset and the switch 74 closed, as shown by the waveforms 56a and 74a. Note that unlike the processing performed by the signals from the microphones 12 and 13, which occurs after the can is struck, the proximity coil performs its sensing when the can is struck. As the can is struck by the coil 15, a part of the energy is coupled through the can 10 to the proximity coil 16. The energy in the coil 16 after being preamplified and rectified is integrated for approximately 0.5 ms by the integrator 76. The results of this integration are sampled and held by the sample-and-hold means 78. When the sound sensed by microphones 12 and 13 is processed, as described in conjunction with FIG. 1, the resultant signal at the output of amplifier 38 is passed through the logarithmic amplifier 81 and the value from the sample-and-hold means 78 is subtracted from this signal. The resultant signal is used as previously described to perform the comparison.

The energy imparted to the can from exciter coil 15 has been found to vary exponentially with the distance between the can 10 and this coil, as mentioned. For this reason, a logarithmic amplifier 81 is employed to linearize this relationship. Moreover, it has been found that the energy delivered to the proximity coil 16 from the can and the resultant signal at the output of the sample-and-hold means 78 varies linearly with the distance between the coil 16 and the can 10. For this reason, this signal is subtracted from the output of the logarithmic amplifier within the differencing amplifier 80. The gain of the loop, which includes the proximity coil, amplifier 69, filter 70, rectifier 72, integrator 76 and sample-and-hold means 78, is set so as to remove the desired component from the signal applied to the amplifier 80 from the amplifier 81. If the can is closer to the coil 15, more energy is sensed by coil 16 and a larger signal is subtracted in amplifier 81. On the other hand, if the can is further from coil 15, a smaller signal is subtracted at amplifier 81. In practice, a variable gain amplifier is employed in this loop allowing a gain adjustment to be made in the environment where the testing occurs.

Thus, an apparatus has been described for detecting dents and deformation in open containers, particularly steel and aluminum cans. The apparatus includes means which provide compensation for background noise and variations in distance between the exciter coil and can.

We claim:

1. An apparatus for detecting defects in an open container comprising:
   striking means for imparting energy to said container to cause it to vibrate at its natural frequencies;
   first sensing means disposed adjacent to said container for sensing said vibrations of said container;
   a first filter for selecting predetermined frequencies associated with a defective one of said containers, coupled to said sensing means;
   comparator means for examining said predetermined frequencies associated with a defective one of said containers, coupled to said filter;
   second sensing means spaced-apart from said container to sense background noise;
   a second filter for selecting said predetermined frequencies associated with a defective one of said containers, coupled to said second sensing means; and,
   cancellation means for cancelling the effects of one signal on a second signal, said cancellation means coupled between said filters and said comparator means so as to minimize the effects of said background noise from the signal applied to said comparator means
   whereby defects in an empty or substantially empty container are detected.

2. The apparatus defined by claim 1 including integration means for integrating the energy associated with said predetermined frequencies, coupled between said first filter and said comparator means.

3. The apparatus defined by claim 2 wherein said striking means comprises magnetic means for providing a magnetic field of a frequency higher than the fundamental frequency of said vibrations.

4. The apparatus defined by claim 1 wherein said first sensing means is a microphone disposed above the opening of said container.

5. An apparatus for detecting defects in an open container comprising:
   striking means for imparting energy to said container to cause vibrations at its natural frequencies;
   a first sensing means disposed adjacent to said container for sensing said vibrations of said container;
   frequency analyzing means for analyzing signals representative of said vibrations and for comparing said signals with a predetermined standard so as to detect defective containers;
   a second sensing means spaced-apart from said first sensing means for sensing background noise;
   cancellation means for cancelling the effect of one signal on another signal, coupled to said first and second sensing means and said frequency analyzing means for removing effects of background noise from said sensed vibrations of said container;
   whereby defective containers may be detected in a noisy environment.

6. The apparatus defined by claim 5 wherein said first sensing means is disposed above the opening of said container.

7. The apparatus defined by claim 5 wherein "a" represents at least a portion of said signals representative of said vibrations and "b" represents at least a portion of a signal representative of said background noise and wherein said cancellation means determines the value $(a^2 - b^2)$.

8. The apparatus defined by claim 5 wherein said frequency analyzer includes a first and second bandpass filter coupled to said first and second sensing means, respectively, a first and a second rectifier coupled to said first and second filters, respectively, and a first and second integrator coupled to said rectifiers, respectively.

9. An apparatus for detecting defects in an open container comprising:
   striking means for imparting energy to said container to cause it to vibrate as its natural frequencies;
   first sensing means disposed adjacent to said container for sensing said vibrations of said container;
   frequency analyzing means for analyzing signals representative of said vibrations and for comparing said signals with a predetermined standard so as to identify defective containers;
   a second sensing means disposed adjacent to said striking means for sensing the energy imparted to said container;
   circuit means coupled to said frequency analyzing means and said second sensing means for providing compensation for variations in distances between said striking means and said container when said energy is imparted to said container;
   whereby compensation is provided for variations in distance between said container and said striking means.

10. The apparatus defined by claim 9 wherein said first sensing means is disposed above the opening of said container.

11. The apparatus defined by claim 9 wherein said circuit means includes a logarithmic amplifier for receiving at least a portion of said signals representative of said vibrations and a differencing means for subtracting at least a portion of said signal from said second sensing means from a signal from said logarithmic amplifier.

12. The apparatus defined by claim 11 wherein said second sensing means comprises a coil.

13. An apparatus for detecting defects in an open container comprising:

striking means for imparting energy to said container to cause it to vibrate at its natural frequencies;

sensing means disposed adjacent to said container for sensing said vibrations of said container;

a filter for selecting predetermined frequencies associated with a defective one of said containers, coupled to said sensing means;

comparator means for examining said predetermined frequencies associated with a defective one of said containers, coupled to said filter;

a coil disposed adjacent to said striking means for detecting said energy imparted to said container by said striking means; and, circuit means coupled to said coil and said comparator means for providing compensation as a function of the energy sensed by said coil;

whereby defects in an empty or substantially empty container are detected.

* * * * *

UNITED STATES PATENT AND TRADEMARK OFFICE
CERTIFICATE OF CORRECTION

PATENT NO. : 4,212,205
DATED : July 15, 1980
INVENTOR(S) : PERRY C. WEST and ROBERT R. BUSS It is certified that error appears in the above-identified patent and that said Letters Patent are hereby corrected as shown below:

Column 6, line 1, "(a-b)(a=b)" should read -(a-b) (a+b)-.

Signed and Sealed this

Thirteenth Day of October 1981

[SEAL]

*Attest:*

GERALD J. MOSSINGHOFF

*Attesting Officer*     *Commissioner of Patents and Trademarks*